United States Patent [19]
Eisch et al.

[11] Patent Number: 6,087,515
[45] Date of Patent: Jul. 11, 2000

[54] METALLOCENES AND PROCESS FOR THE PREPARATION OF METALLOCENES

[75] Inventors: John J. Eisch, Vestal, N.Y.; Yun Qian, North Wales, Pa.; Jürgen Weber, Vestal, N.Y.; Nicola Zandona, Waterloo; Fabian Siberdt, Brussels, both of Belgium

[73] Assignee: Solvay Polyolefins Europe-Belgium (Societe Anonyme), Brussels, Belgium

[21] Appl. No.: 09/167,597

[22] Filed: Oct. 7, 1998

[51] Int. Cl.⁷ .............................. C07F 17/00; C07F 7/00
[52] U.S. Cl. ................... 556/52; 556/5; 502/103; 502/117; 526/160; 526/943
[58] Field of Search .............. 556/52, 54; 502/103, 502/117; 526/160, 943

[56] References Cited

U.S. PATENT DOCUMENTS 5,158,920  10/1992  Razavi ................................ 502/152

FOREIGN PATENT DOCUMENTS

| | | |
|---|---|---|
| 0416815A2 | 3/1991 | European Pat. Off. |
| WO 92/00333 | 1/1992 | WIPO |
| WO 92/05203 | 4/1992 | WIPO |
| WO 94/03506 | 2/1994 | WIPO |

*Primary Examiner*—Porfirio Nazario-Gonzalez
*Attorney, Agent, or Firm*—Venable

[57] ABSTRACT

A metallocene corresponding to the formula

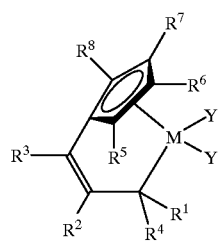

wherein M is a group 4 transition metal,
each Y is, independently, selected from the group of halogen, hydrocarbyl and hydrocarbyloxy,
$R^1$, $R^4$ are, independently, selected from the group of hydrogen, hydrocarbyl, hydrocarbyloxy,
$R^2$, $R^3$, $R^5$, $R^6$, $R^7$, $R^8$ are, independently, selected from the group of hydrogen, hydrocarbyl, hydrocarbyloxy, with the provision that, respectively, $R^2$ and $R^3$, $R^5$ and $R^6$, $R^7$ and $R^8$ can be linked to each other.

A process for the preparation of metallocenes comprising the following steps:
(a) contacting, in a solvent, a transition metal halide of formula $MX_4$ with an organometallic compound of formula $M'R_m$, wherein M is a group 4 transition metal, X is a halogen, M' is an element chosen from the groups 1, 2 and 13 of the periodic table, R is hydrogen, an alkyl, aryl, alkenyl or alkynyl group containing up to 20 carbon atoms, m=1 when M' is a group 1 element, m=2 when M' is a group 2 element, m=3 when M' is a group 13 element, in order to reduce M, which leads to a subvalent transition metal halide, (b) purifying the subvalent transition metal halide and (c) contacting the subvalent transition metal halide with at least one fulvene compound.

3 Claims, No Drawings

METALLOCENES AND PROCESS FOR THE PREPARATION OF METALLOCENES

TECHNICAL FIELD

The present invention relates to metallocenes useful as catalyst in the polymerization of olefins and to a process for the preparation of metallocenes.

BACKGROUND OF THE INVENTION

Metallocenes for the polymerization of olefins have been known for several years. European Patent Application EP 0416815 discloses constrained geometry metal complexes comprising a single cyclopentadienyl group and at least an heteroatom Y chosen from —O—, —S—, —NR—, —PR—.

These metallocenes have been synthesized by contacting a tetravalent metal reactant and a group 1 derivative or Grignard derivative of the cyclopentadienyl compound.

Methods for the preparation of metallocenes for the polymerization of olefins generally involve some variant of the reaction of a substituted cyclopentadienylalkali-metal salt with a transition metal halide in the proper molar ratio to produce the desired number of ligands to the transition metal. For instance, the U.S. Pat. No. 5,158,920 describes the preparation of isopropylidene (cyclopentadienyl-9-fluorenyl) zirconium dimethyl by deprotonation of fluorene (using methyllithium as deprotonating agent) to obtain the ionic species fluorenyl lithium, followed first by the ligand forming reaction with 6,6 dimethylfulvene, and then by the reaction with zirconium tetrachloride to form the metallocene.

These known methods are carried out under particular conditions incompatible with usual polymerization conditions. Consequently, the known methods cannot be carried out "in situ" in the polymerization reactor but have to be carried out separately. In most cases the metallocenes obtained by these known methods have to be separated from the reaction mixture and stored under special conditions. Additionally, the known methods do not present a high productivity and a high selectivity.

SUMMARY OF THE INVENTION

It is an object of the present invention to solve the aforementioned problems by providing a novel process for the preparation of metallocenes presenting a high productivity and a high selectivity and which can be carried out "in situ". Another object of the present invention is to provide a process permitting the preparation of new metallocenes. Still another object of the invention is to provide novel metallocenes. A further object is to provide for the use of the said novel metallocenes in the polymerization of olefins.

The invention is thus related to metallocenes corresponding to the formula (I)

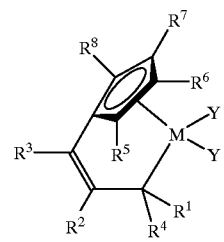

wherein M is a group 4 transition metal each Y is selected, independently, from the group of halogen, hydrocarbyl and hydrocarbyloxy, $R^1$, $R^4$ are, independently, selected from the group of hydrogen, hydrocarbyl, hydrocarbyloxy, $R^2$, $R^3$, $R^5$, $R^6$, $R^7$, $R^8$ are, independently, selected from the group of hydrogen, hydrocarbyl, hydrocarbyloxy, with the provision that, respectively, $R^2$ and $R^3$, $R^5$ and $R^6$, $R^7$ and $R^8$ can be linked to each other.

The invention is further related to a process for the preparation of metallocenes comprising the following steps:

(a) contacting, in a solvent, a transition metal halide of formula $MX_4$, wherein M is a group 4 transition metal and X is a halogen, with an organometallic compound of formula $M'R_m$, wherein M' is an element chosen from the groups 1, 2 and 13 of the periodic table, R is hydrogen, an alkyl, aryl, alkenyl or alkynyl group containing up to 20 carbon atoms, m=1 when M' is a group 1 element, m=2 when M' is a group 2 element, m=3 when M' is a group 13 element, in order to reduce M, which leads to a subvalent transition metal halide of formula $MX_2$, (b) purifying the transition metal halide $MX_2$ obtained in (a) in order to eliminate the products of formula $M'X_m$ formed during the step (a), (c) contacting the purified subvalent transition metal halide of formula $MX_2$ obtained in (b) with at least one fulvene compound in order to obtain a metallocene.

DETAILED DESCRIPTION

All references to the Periodic Table of Elements herein refer to the version published in CRC Handbook of Chemistry and Physics, 77th Edition, 1996/97; the notation used being the new IUPAC notation of groups.

According to a first aspect, the present invention relates to novel metallocenes corresponding to formula (I) wherein M is a group 4 transition metal, each Y is selected, independently, from the group of halogen, hydrocarbyl and hydrocarbyloxy, $R^1$, $R^4$ are, independently, selected from the group of hydrogen, hydrocarbyl, hydrocarbyloxy, and $R^2$, $R^3$, $R^5$, $R^6$, $R^7$, $R^8$ are, independently, selected from the group of hydrogen, hydrocarbyl, hydrocarbyloxy, with the provision that, respectively, $R^2$ and $R^3$, $R^5$ and $R^6$, $R^7$ and $R^8$ can be linked to each other. By hydrocarbyl are designated those groups containing hydrogen and carbon atoms, such as alkyl, aryl, alkenyl, allyl, alkynyl, cycloalkyl groups; by hydrocarbyloxy are designated those groups containing hydrogen, carbon and oxygen atoms, such as alkoxy or acetyl groups.

Suitable hydrocarbyl and hydrocarbyloxy groups will contain from 1 to 20 carbon atoms. Preferably, $R^1$, $R^4$, $R^2$, $R^3$, $R^5$, $R^6$, $R^7$, $R^8$ are selected from the group of hydrogen and hydrocarbyl. Preferred hydrocarbyl groups are those containing from 1 to 12 carbon atoms and include straight and branched alkyl, alkenyl, allyl and alkynyl radicals, cyclic hydrocarbon radicals, alkyl-substituted cyclic hydrocarbon radicals, aromatic radicals and alkyl substituted aromatic radicals. Moreover, groups $R^2$ and $R^3$, groups $R^5$ and $R^6$, groups $R^7$ and $R^8$, respectively, can be linked to each other forming a fused ring system which may be fully or partially saturated or unsaturated. For example groups $R^2$ and $R^3$, groups $R^5$ and $R^6$, groups $R^7$ and $R^8$, respectively, can jointly be a divalent polyalkylene group —$(CH_2)_n$— where n is a number from 1 to 20 or a divalent polyvinylene group —$(CH=CH)_n$—.

In the metallocenes according to the invention, each Y is, independently, selected from the group of halogen, hydrocarbyl and hydrocarbyloxy. Suitable hydrocarbyl and hydrocarbyloxy groups will contain from 1 to 20 carbon atoms, preferably from 1 to 10 carbon atoms. Y is preferably a halogen, and more specifically chlorine. Especially preferred are metallocenes where the two Y groups are identical.

In the metallocenes according to the invention, the transition metal M is preferably chosen from titanium and zirconium.

Good results have been obtained with metallocenes wherein $R^4$, $R^5$, $R^6$, $R^7$ and $R^8$ are hydrogen atoms and $R^1$, $R^2$ and $R^3$ are selected from hydrogen and hydrocarbyl, with the provision that $R^2$ and $R^3$ can be linked together. Preferred metallocenes are those wherein $R^4$, $R^2$, $R^3$, $R^5$, $R^6$, $R^7$, $R^8$ are hydrogen atoms and wherein $R^1$ is a hydrocarbyl radical, more preferably an aromatic radical. Especially preferred is a metallocene wherein M is Ti or Zr, Y is a halogen atom, $R^2$, $R^3$, $R^4$, $R^5$, $R^6$, $R^7$ and $R^8$ are hydrogen atoms and $R^1$ is a phenyl group.

According to a second aspect, the present invention relates to a process for the preparation of metallocenes comprising the following steps:
(a) contacting, in a solvent, a transition metal halide of formula $MX_4$, wherein M is a group 4 transition metal and X is a halogen, with an organometallic compound of formula $M'R_m$, wherein M' is an element chosen from the groups 1, 2 and 13 of the periodic table, R is hydrogen, an alkyl, aryl, alkenyl or alkynyl group containing up to 20 carbon atoms, m=1 when M' is a group 1 element, m=2 when M' is a group 2 element, m=3 when M' is a group 13 element, in order to reduce M, which leads to a subvalent transition metal halide of formula $MX_2$,
(b) purifying the transition metal halide $MX_2$ obtained in (a) in order to eliminate the products of formula $M'X_m$ formed during the step (a),
(c) contacting the purified subvalent transition metal halide of formula $MX_2$ obtained in (b) with at least one fulvene compound in order to obtain a metallocene.

The solvent used in step (a) is generally a polar solvent. Aprotic polar solvents are convenient. Good results have been obtained with ethers and glycol ethers. Tetrahydrofuran is preferred. It is further recommended that this first step is conducted at a low temperature of at least −100° C., the temperatures of at least −90° C. being preferred. The temperature is generally at most 0° C., in particular at most −20° C. The formation of the subvalent transition metal halide is generally instantaneous. The duration of step (a) does currently not exceed 10 min, in particular it lasts at most 5 min. The duration of step (a) is generally at least 30 s, in particular at least 1 min. After completion of the reaction it may be useful to bring the reaction mixture to room temperature and to stir it at room temperature during at least 1 h, in particular at least 2 h. The duration of this additional stirring step is generally at most 48 h, in particular at most 24 h.

In the transition metal halide of formula $MX_4$ used in step (a) of the preparation process according to the invention, M is preferably titanium or zirconium. X is preferably chlorine.

The organometallic compound of formula $M'R_m$ used in step (a) comprises advantageously as R group those containing from 2 to 8 carbon atoms, especially from 2 to 6 carbon atoms. Alkyl groups are preferred, especially linear alkyl groups. n-Butyl is often used. M' is advantageously chosen from lithium, magnesium and aluminum. Especially preferred is lithium. Good results have been obtained with n-butyllithium.

The quantities of reagents used in step (a) of the present invention are usually such that the molar ratio of the organometallic compound to the transition metal halide is at least 0.1, in particular 0.5, molar ratios of at least 1 are especially preferred. The molar ratio is commonly at most 10, in particular 8, values of at most 4 are often used. A molar ratio of about 2 is recommended.

The reaction mixture containing the subvalent transition metal compound of formula $MX_2$ obtained at the end of step (a) is then submitted to a purification step (b) in order to eliminate the products of formula $M'X_m$ formed during the step (a). During step (b) at least 50% by weight of the by-products of formula $M'X_m$ are eliminated from the subvalent transition metal. Preferably at least 80% by weight of these by-products are eliminated. Especially good results have been obtained when at least 90% by weight of the by-products of formula $M'X_m$ formed during the step (a) are eliminated from the subvalent transition metal compound. It has been established that the by-products of formula $M'X_m$ formed in reaction of step (a) constitute a disturbing factor in the further use of the subvalent transition metal halide for the preparation of metallocenes and also when the metallocene is further used for the polymerization of olefins. Any purification method suitable for the elimination of these by-products can be used. A suitable method comprises the evaporation of the solvent followed by the extraction of the residue with a solvent of the subvalent transition metal halide and elimination of the suspended by-product of formula $M'X_m$ by filtration.

Step (c) of the present invention is usually carried out at a temperature of at least 0° C., especially of at least 20° C. The temperature is commonly at most 50° C., in particular at most 30° C. The duration of step (c) of the present invention is generally at least 10 s, in most cases at least 1 min. The duration is commonly at most 5 h, in particular at most 2 h.

Step (c) can optionally be followed, in order to obtain a maximum conversion, by a stirring step at a temperature of at least 20° C. lower than the boiling temperature of the reaction mixture of step (c) up to the boiling temperature of this reaction mixture. The duration of this stirring step is commonly at least 1 h, in particular at least 2 h. The duration is generally at most 24 h, in particular at most 15 h.

Step (c) of the present invention is advantageously carried out in the presence of a solvent. Aromatic hydrocarbon liquids are convenient. Monocyclic aromatic hydrocarbons and their substituted derivatives such as benzene and toluene are preferred. Toluene is especially preferred.

The preparation process according to the invention is advantageously applied to the preparation of the novel metallocenes according to the invention. In this case, a single fulvene compound is used in step (c) which corresponds to the formula

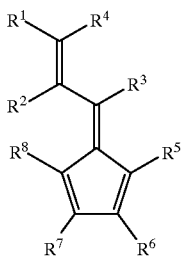

in which $R^1$, $R^4$, $R^2$, $R^3$, $R^5$, $R^6$, $R^7$, $R^8$ are, independently, selected from the group of hydrogen, hydrocarbyl, hydrocarbyloxy such as defined here above in relation with the metallocenes according to the invention, with the provision that, respectively, $R^2$ and $R^3$, $R^5$ and $R^6$, $R^7$ and $R^8$ can be linked to each other.

Suitable hydrocarbyl and hydrocarbyloxy groups will contain from 1 to carbon atoms. Preferably, $R^1$, $R^4$, $R^2$, $R^3$, $R^5$, $R^6$, $R^7$, $R^8$ are selected from the group of hydrogen and hydrocarbyl. Preferred hydrocarbyl groups are those containing from 1 to 12 carbon atoms and include straight and branched alkyl, alkenyl, allyl and alkynyl radicals, cyclic hydrocarbon radicals, alkyl-substituted cyclic hydrocarbon radicals, aromatic radicals and alkyl substituted aromatic radicals. Moreover, groups $R^2$ and $R^3$, groups $R^5$ and $R^6$, groups $R^7$ and $R^8$, respectively, can be linked to each other forming a fused ring system which may e fully or partially saturated or unsaturated. For example groups $R^2$ and $R^3$, groups $R^5$ and $R^6$, groups $R^7$ and $R^8$, respectively, can jointly be a divalent polyalkylene group —$(CH_2)_n$— where n is a number from 1 to 20 or a divalent polyvinylene group —$(CH=CH)_n$—.

Good results have been obtained with a fulvene compound wherein $R^1$ is selected from the group of hydrogen and hydrocarbyl, $R^4$, $R^5$, $R^6$, $R^7$ and $R^8$ are hydrogen atoms and $R^2$ and $R^3$ are, independently, selected from the group of hydrogen, hydrocarbyl with the provision that $R^2$ and $R^3$ can be linked to each other. Very good results have been obtained with a fulvene compound wherein $R^2$, $R^3$, $R^4$, $R^5$, $R^6$, $R^7$ and $R^8$ are hydrogen atoms and $R^1$ is a phenyl group.

The fulvene compound is generally used in step (c) in such a quantity that the molar ratio of fulvene compound to the subvalent transition metal halide is at least 0.1, in particular at least 0.5. The molar ratio is commonly at most 2, in particular at most 1.

According to a variant of the preparation process according to the invention, the transition metal halide used in step (a) or the purified subvalent transition metal halide obtained after step (b) can be deposited on an inert support. This support can be chosen from polymeric and inorganic supports. Inorganic supports are preferred. Examples of inorganic supports are mineral oxides (such as silica, alumina, titania, zirconia, thoria) and their mixtures, and mixed oxides (such as aluminium silicate and aluminium phoshate). Silica is preferred. The supported transition metal halide or subvalent transition metal halide can be obtained in any known adequate manner. For instance, the support can be impregnated with a solution of the transition metal halide or the subvalent transition metal halide.

The preparation process according to the invention permits the preparation of metallocenes in a very good yield. These metallocenes are substantially free of by-products of formula $M'X_m$. An important advantage of the preparation process according to the invention resides in the simplicity of step (c). Although the process exhibits simplicity, it can however lead to a large variety of different types of bridged metallocenes. Indeed, according to the nature of the substituents on the carbon atom in position 6 of fulvene, the nature of the bridge can be varied. Another important advantage of the preparation process according to the present invention resides in the possibility of carrying out step (c) "in situ". Since the reaction of step (c) is very rapid and can occur under normal polymerization conditions in the presence of an olefin; it can be carried out in the polymerization reactor or in a conditioning reactor disposed before the polymerization reactor. The reaction of step (c) is further characterized by a high productivity and a high selectivity.

The process according to the invention is suitable for the preparation of the novel metallocenes according to the invention described here above wherein Y is a halogen atom. The metallocenes wherein one or both of the Y groups is a hydrocarbyl or a hydrocarbyloxy group can be obtained by reacting these metallocenes with a reagent capable of substituting the halogen atoms by a hydrocarbyl or a hydrocarbyloxy group. Such reagents are well known in the art. Examples are organometallic compounds of lithium, magnesium, zinc, aluminium or tin. Generally organoaluminum compounds and in particular trialkylaluminum compounds are used.

The metallocenes according to the invention are useful as catalysts for the polymerization of olefins. These metallocenes can be used as such or can be supported on an inert support as defined here above. They can be used in combination with aluminoxanes which can be chosen from linear aluminoxanes or from the cyclic aluminoxanes. Methylaluminoxane is preferred. They can also be used in combination with an ionizing agent. This ionizing agent can be chosen from the compounds comprising a first part which has the properties of a Lewis acid and which is capable of ionizing the metallocene and a second part which is inert towards the ionized metallocene. Examples of ionizing agents are triphenylcarbenium tetrakis(pentafluorophenyl)borate, N,N-dimethylanilinium tetrakis(pentafluorophenyl)borate, tri(n-butyl)ammonium tetrakis(pentafluorophenyl)-borate, tri(pentafluorophenyl)borane, triphenylborane, trimethylborane, tri(trimethylsilyl)-borane and organoboroxines. The ionizing agent is preferably triphenylcarbenium tetrakis(pentafluorophenyl)borate. Organometallic compounds are generally used as cocatalysts. They may be selected from organometallic compounds of lithium, magnesium, zinc, aluminium or tin. The best results are obtained with organoaluminum compounds and in particular with trialkylaluminum compounds.

The olefins can be chosen from those containing up to 20, preferable up to 12, carbon atoms par molecule. The olefin is preferably ethylene or propylene.

The metallocenes obtained according to the process of the invention may be used for the homopolymerization of one of the olefins or for the copolymerization of one of the olefins with one or more comonomers. The preferred comonomers of ethylene are butene, hexene and their mixtures. The preferred comonomers of propylene are ethylene, butene, and their mixtures.

EXAMPLES a) Preparation of 6-(β-trans-Styryl)fulvene from trans-Cinnamaldehyde and Cyclopentadiene

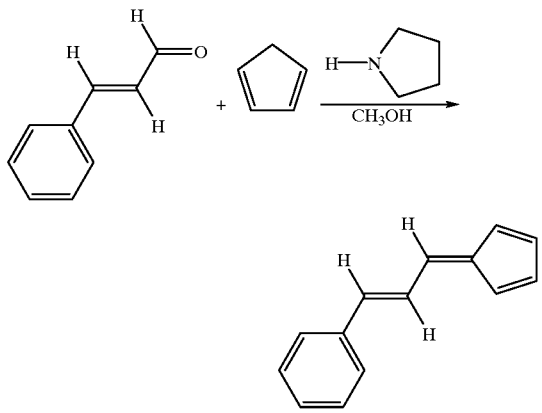

A solution of 20.4 mL (0.16 mol) of trans-cinnamaldehyde and 33 mL (0.40 mol) of freshly-distilled cyclopentadiene in 200 mL of reagent-grade methanol was prepared. The mixture was cooled with an ice bath, and 20 mL (0.24 mol) of pyrrolidine were slowly added. The temperature was allowed to rise to room temperature and the reaction mixture was stirred overnight. A 15 mL portion of acetic acid (0.26 mol) were added to the dark red slurry, followed by 0.4 L of ether and 0.4 L of water. The organic layer was separated and the aqueous layer was extracted with four 100-mL portions of ether. The combined organic liquids were washed with two portions of 250 mL of water and two portions of 150 mL of NaCl solution and finally dried over magnesium sulfate. The solution was concentrated to afford a mixture of red crystals and a red oil which was stored in the freezer overnight. The crystals were separated through suction filtration and were washed with small portions of cold methanol in order to remove adhering oil residues. The product was dried under oil-pump vacuum for 4 hours and stored under argon in the freezer. Yield: 15.4 g (85.5 mmol) 54%.

The crystallized material was used for the following experiments.

b) Preparation of Zirconium (II) Chloride Bis (Tetrahydrofuran)—Lithium Chloride Free Under argon and moisture-free conditions, 6.32 (27.1 mmol) of zirconium (IV) chloride were cooled to −78° C., and 175 mL of THF were slowly added. After addition the milky slurry was allowed to warm up to room temperature and was stirred for 45 minutes. At this point, 50 mL of toluene were added and the mixture was cooled again to −78° C. Then, over a period of 30 min, 36 mL of a 1.6 M solution of n-butyllithium in hexane was gradually introduced. The suspension turned from white to yellow and then gradually to dark brown. The reaction mixture was allowed to warm up to room temperature and was stirred for 18 hours. The removal of the lithium chloride was accomplished as follows: As much of the THF as possible was evaporated under reduced pressure and collected in a cooled dry ice trap. During this process the flask with the zirconium (II) chloride solution was kept at about 25° C. The amount of solvent removed was 194 mL.

After evaporation of the THF the remaining toluene slurry was cooled with an acetone dry-ice bath and kept at this temperature for about 10–15 minutes for completion of the lithium chloride precipitation. An inert gas filtration set-up was assembled, consisting of a filter with a side arm to equalize pressure and a porosity of the frit of 10 to 20 microns. This filter was fitted with a Schlenk flask for collection of the zirconium (II) chloride solution. The slurry was allowed to warm up to room temperature again and was immediately cannulated through a Teflon tube into the fritted filter. The reaction flask and thus the filter residue were washed with two portions of 25 mL of toluene/THF mixture (4/1). The filter residue wad dried on the filter under vacuum and weighed. 2.09 g (49.3 mmol) of light brown powdery lithium chloride were found—that is 91% of the theoretically expected amount. The range of the lithium chloride collected varied between 85% and 101% over a number of trials. When the value was below 90%, a second filtration was performed in order to remove more of the lithium chloride.

c) Reaction of Zirconium (II) Chloride with 6-(β-trans-Styryl)fulvene

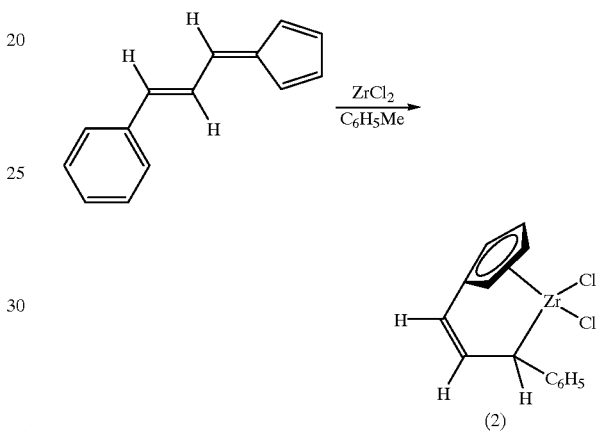

To the toluene solution of zirconium (II) chloride 3.42 g (19 mmol) of solid 6-(β-trans-Styryl)fulvene were added. The mixture was stirred overnight and then heated in an oil bath to 70 to 85° C. for three hours. A small sample was drawn from the solution and the solvents were evaporated. The vacuum-dried sample dissolved with benzene-$d_6$ and was analyzed by NMR spectroscopy. The spectrum showed that all of the fulvene had been consumed. The bulk of the toluene suspension was filtered and the filtrate was collected. The solvents were completely evaporated. The solid was slurried with 40 mL of pentane and stirred for 3 hours. The solids were allowed to settle and the pentane layer was cannulated off. The remaining solids were then dissolved in 50 mL of toluene and another filtration was performed. The filtrate was stored in the freezer for precipitation of the tan-colored product. 1.8 g of the metallocene of formula (2) were collected. By subjecting this product to a Soxhlet extraction with boiling hexane this metallocene could be isolated from the extract as a white powder. However, the $^1$H and $^{13}$C NMR spectra of the tan-colored product and this white powder were identical.

Characterization of metallocene of formula (2)
  a. Elemental analysis
  1. Calculated for $C_{14}Cl_2H_{12}Zr$: Zr, 26.58%; Cl, 20.66%;
  2. Found: Zr, 26.75%; Cl, 20.56%.
  b. Nuclear magnetic resonance data
  1. $^1$H NMR(360 MHz,$C_6D_6$), δ:7.20–7.00(m,Ph-H), 6.79–6.75(m, 1H), 6.67–6.63(m, 1H), 6.49–6.45(m, 1H), 6.45–6.41(m, 1H), 6.33–6.08(m, 4H), 5.98–5.94 (m, 1H), 5.81–5.77(m, 1H), 5.76–5.72(m, 1H), 5.68–5.64(m, 1H), 3.92–3.88(m, 1H), 3.54–3.50(m, 1H)

2. $^{13}$C NMR(90.6 MHz, $C_6D_6$), δ: 136.98(s), 134.90(s), 134.48(s), 16 CH— peaks between 134 and 120, 112.92(d), 110.74(d), 110.32(d), 106.04(d), 50.80(d), 50.34(d).

3. By a DEPT experiment on the $^1$H NMR spectrum, it was established that the multiplets at 3.88–3.92 and at 3.50–3.54 ppm arise from isomeric benzylic C-H groups that are coupled with vinylic protons in the 6.33 and the 6.10 ppm regions respectively. These data support the existence of this metallocene in two isomeric forms, 2a and 2b, due to a twist in the three-carbon pendant chain:

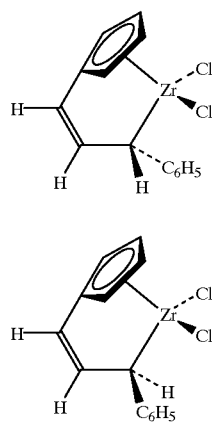

c. Mass spectrum (70 eV, direct insertion sample):

M-Cl: 308 and 306 in a 3:1 intensity ratio.

d) Polymerization

Run 1: A 3 l polymerization reactor was filled with 704 mg of MAO (10% wt solution in toluene), then with 1l of isobutane. The temperature was raised to 80° C. and ethylene was added until a partial pressure of 10 bar in ethylene was obtained. 5.2 mg of the metallocene catalyst of formula (2) obtained in step c) was mixed with 704 mg of MAO for 15 min and then added to the polymerization reactor in order to start the polymerization. The temperature and the ethylene pressure were kept constant during the polymerization. After 60 minutes, the polymerization was stopped by degassing the reactor. The polyethylene was collected. The quantities and properties of the obtained polyethylene are described in table I.

Run 2R (not according to the invention):

In this run the polymerization was conducted in the same conditions as run 1 except that 10 mg of a metallocene catalyst of formula (2) was used which was prepared by a preparation process using a zirconium (II) chloride which was not purified and which contained the lithium chloride by-product formed during step b) described here above. The quantities and properties of the obtained polyethylene are described in table I.

Run 3: In this run the polymerization was conducted in the same conditions as run 1 except that hydrogen (partial pressure 0.1 bar) was added to the polymerization reactor.

Run 4: A 3 l polymerization reactor was filled with 1 mmol trimethylaluminum TMA (10% wt solution in hexane), then with 1 l of isobutane. The temperature was raised to 50° C. and ethylene was added until a partial pressure of 10 bar in ethylene was obtained. 5.2 mg of the metallocene catalyst of formula (2) obtained in step c) and 1 mole equivalent of triphenylcarbenium tetrakis (pentafluorophenyl)borate (relative to Zr) were then added to the polymerization reactor in order to start the polymerization. The temperature and the ethylene pressure were kept constant during the polymerization. After 60 minutes, the polymerization was stopped by degassing the reactor. The polyethylene was collected. The quantities and properties of the obtained polyethylene are described in table I.

Run 5: In this run the polymerization was conducted in the same conditions as run 4 except that hydrogen (partial pressure 0.2 bar) was added to the polymerization reactor.

TABLE I

| Run | Productivity (kg PE/mmol Zr) | solubles (g/kg PE) | $MI_2$ (g/10 min) | HLMI (g/10 min) |
|---|---|---|---|---|
| 1 | 13.0 | 3.1 | <0.1 | 1.8 |
| 2R | 5.7 | 4.3 | <0.1 | 1.0 |
| 3 | 10.1 | 5.6 | 0.5 | 360 |
| 4 | 3.6 | n.a. | n.a. | n.a. |
| 5 | 0.9 | n.a. | n.a. | n.a. |

What is claimed is:

1. A metallocene corresponding to the formula

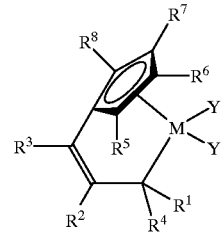

wherein M is a group 4 transition metal each Y is, independently, selected from the group of halogen, hydrocarbyl and hydrocarbyloxy, $R^1$, $R^4$ are, independently, selected from the group of hydrogen, hydrocarbyl, hydrocarbyloxy, $R^2$, $R^3$, $R^5$, $R^6$, $R^7$, $R^8$ are, independently, selected from the group of hydrogen, hydrocarbyl, hydrocarbyloxy, with the provision that, respectively, $R^2$ and $R^3$, $R^5$ and $R^6$, $R^7$ and $R^8$ can be linked to each other.

2. Metallocene according to claim 1, wherein $R^1$, $R^2$ and $R^3$ are selected from the group of hydrogen and hydrocarbyl and $R^4$, $R^5$, $R^6$, $R^7$, $R^8$ are hydrogen atoms.

3. Metallocene according to claim 1, wherein M is Ti or Zr, Y is a halogen atom, $R^2$, $R^3$, $R^4$, $R^5$, $R^6$, $R^7$ and $R^8$ are hydrogen atoms and $R^1$ is a phenyl group.

* * * * *